US012749054B1

(12) United States Patent
Ezell et al.

(10) Patent No.: US 12,749,054 B1
(45) **Date of Patent: *Sep. 29, 2026**

(54) PHARMACEUTICAL RETURNS PROCESSING SYSTEM AND RELATED METHODS

(71) Applicant: Inmar Rx Solutions, Inc., Ft. Worth, TX (US)

(72) Inventors: Daniel Ezell, Buffalo Grove, IL (US); Erin Pietranek, Gurnee, IL (US)

(73) Assignee: INMAR RX SOLUTIONS, INC., Ft. Worth, TX (US)

( * ) Notice: Subject to any disclaimer, the term of this patent is extended or adjusted under 35 U.S.C. 154(b) by 442 days.

This patent is subject to a terminal disclaimer.

(21) Appl. No.: 18/236,351

(22) Filed: Aug. 21, 2023

(51) Int. Cl.

| | |
|---|---|
| ***G16H 20/13*** | (2018.01) |
| ***G06K 7/14*** | (2006.01) |
| ***G06Q 10/30*** | (2023.01) |
| ***G06Q 20/10*** | (2012.01) |

(52) U.S. Cl.
CPC ......... *G06Q 20/102* (2013.01); *G06K 7/1404* (2013.01); *G06Q 10/30* (2013.01); *G16H 20/13* (2018.01)

(58) Field of Classification Search
CPC .... G06Q 20/102; G06Q 10/30; G06Q 30/016; G06Q 20/4016; G06Q 20/407; G06Q 30/0281; G16H 20/13; G06K 7/1404
See application file for complete search history.

(56) References Cited

U.S. PATENT DOCUMENTS

| | | | | |
|---|---|---|---|---|
| 5,884,806 | A * | 3/1999 | Boyer et al. | A61J 7/02 |
| 6,535,637 | B1 * | 3/2003 | Wootton et al. | B65B 57/00 |
| 8,215,540 | B2 * | 7/2012 | Szesko | G16H 20/13 235/475 |
| 11,481,739 | B1 * | 10/2022 | McKinzie | G06Q 10/30 |
| 2008/0195247 | A1 * | 8/2008 | Mallett | G07F 11/62 700/231 |
| 2014/0207600 | A1 * | 7/2014 | Ezell | G16H 20/10 705/26.1 |
| 2017/0199983 | A1 * | 7/2017 | Cano | A61J 7/02 |
| 2018/0025334 | A1 * | 1/2018 | Pourfallah | G06Q 20/14 705/41 |
| 2018/0165421 | A1 * | 6/2018 | Hall et al. | G07F 9/001 |
| 2020/0135315 | A1 * | 4/2020 | Ripley et al. | G06Q 10/30 |
| 2020/0342422 | A1 | 10/2020 | Ezell | |
| 2022/0138762 | A1 * | 5/2022 | Flores et al. | G06Q 30/016 |
| 2023/0169473 | A1 * | 6/2023 | Okuda | G06Q 10/087 705/308 |

* cited by examiner

*Primary Examiner* — Jessica Lemieux
(74) *Attorney, Agent, or Firm* — ALLEN, DYER, DOPPELT, GILCHRIST, P.A. Attorneys at Law

(57) ABSTRACT

A pharmaceutical returns processing system may include a pharmaceutical returns processing device configured to acquire an image of an adjacent serialized medication having a unique medication serial identifier thereon. The pharmaceutical returns processing system may also include a pharmaceutical returns processing server configured to apply optical image recognition to the image to determine the unique medication serial identifier, determine a return payment corresponding to the unique medication serial identifier, and process the return payment.

18 Claims, 5 Drawing Sheets

PHARMACEUTICAL RETURNS PROCESSING SYSTEM AND RELATED METHODS

TECHNICAL FIELD

The present invention relates to the field of pharmaceuticals, and, more particularly, to pharmaceutical returns and related methods.

BACKGROUND

Serialization of a medication is the assignment of a unique serial number to each salable medication product. The unique serial number of each medication product may be used to obtain information about the medication. For example, the unique serial number may be used to identify the medication, the origin of the medication, the batch number of the medication, and the medication processing date, for example.

It may be undesirable for an unused, unwanted, or expired medication to be misplaced. For example, a misplaced medication may be mistaken for another medication or may be accidentally used or intentionally misused by someone other than the intended user of the medication.

U.S. Patent Application Publication No. 2020/0135315 to Ripley et al., is directed to unsaleable pharmaceutical item handling and disposal systems. A device may include at least one camera, a display device, and a processor coupled to the camera and the display device. The camera may be configured to capture first optical data of a unsaleable pharmaceutical item and second optical data of an operator. The processor may be configured to provide a graphical interface to the display device. The graphical interface may include information to guide the operator through a process of sorting unsaleable pharmaceutical items for disposal, the graphical interface including the first optical data and the second optical data.

U.S. Pat. No. 10,733,578 to Ezell is directed to a method of management of return items. More particularly, Ezell discloses a method for collecting returned items or information about returned items and evaluating return policy criteria with respect to collected items, and a system for the same, are disclosed. The method includes providing a station, such as a kiosk terminal, preferably at a pharmacy location. The station includes a computer and a user interface including a touch screen interface. Items, for example, pharmaceutical items to be returned are brought to the station. The user enters information at the station, such as by scanning a bar code on a container of the item, weighing the item or its contents, and entering lot number and expiration date associated with the item. A system and method for facilitating recalls is also provided.

SUMMARY

A pharmaceutical returns processing system may include a pharmaceutical returns processing device configured to acquire an image of an adjacent serialized medication having a unique medication serial identifier thereon. The pharmaceutical returns processing system may also include a pharmaceutical returns processing server configured to apply optical image recognition to the image to determine the unique medication serial identifier, determine a return payment corresponding to the unique medication serial number, and process the return payment.

The pharmaceutical returns processing device may include a controller and a camera coupled thereto to acquire the image of the serialized medication. The pharmaceutical returns processing device may include a housing defining a return medication placement area for placement of the serialized medication, and a camera carried by the housing and having the return medication placement area within a field of view of the camera, for example.

The pharmaceutical returns processing device may include a display carried by the housing. The pharmaceutical returns processing server may be configured to cooperate with the pharmaceutical returns processing device to prompt, via the display, a user to provide input to accept the return payment, and process the return payment based upon the input indicative of acceptance of the return payment, for example.

The pharmaceutical returns processing server may be configured to apply optical image recognition to the image to determine at least one of a shape and a color of the serialized medication, and determine the return payment based thereon, for example. The pharmaceutical returns processing server may be configured to apply optical image recognition to the image to determine a quantity of the serialized medication, and determine the return payment based upon the quantity.

The serialized medication may include at least one serialized pill having the unique medication serial identifier thereon, for example. The serialized medication may include a serialized medication container having the unique medication serial identifier thereon, for example.

The unique medication serial identifier may include a machine readable unique medication serial identifier code. The pharmaceutical returns processing server may be configured to be switchable between a returns mode for determining the return payment, and a dispensing mode for dispensing a dispensed medication, for example.

The pharmaceutical returns processing device may include a gate and a controller coupled thereto. The controller may be configured to, in the dispensing mode, operate the gate to dispense the dispensed medication, and in the returns mode, acquire the image of the adjacent serialized medication, for example. The pharmaceutical returns processing server may be configured to process the return payment in real time.

A method aspect is directed to a method of processing a pharmaceutical return. The method may include using a pharmaceutical returns processing server to apply optical image recognition to an image to determine a unique medication serial identifier. The image may be acquired by a pharmaceutical returns processing device and may be of an adjacent serialized medication having the unique medication serial identifier thereon. The method may include using the pharmaceutical returns processing server to determine a return payment corresponding to the unique medication serial number, and process the return payment.

A computer readable medium aspect is directed to a non-transitory computer readable medium for processing a pharmaceutical return. The non-transitory computer readable medium has computer executable instructions that when executed by a processor cause the processor to perform operations. The operations may include applying optical image recognition to an image to determine a unique medication serial identifier, the image being acquired by a pharmaceutical returns processing device and being of an adjacent serialized medication having the unique medication serial identifier thereon. The operations may include determining a return payment corresponding to the unique medication serial number, and processing the return payment.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to indicate similar elements in alternative embodiments.

Figure 1:
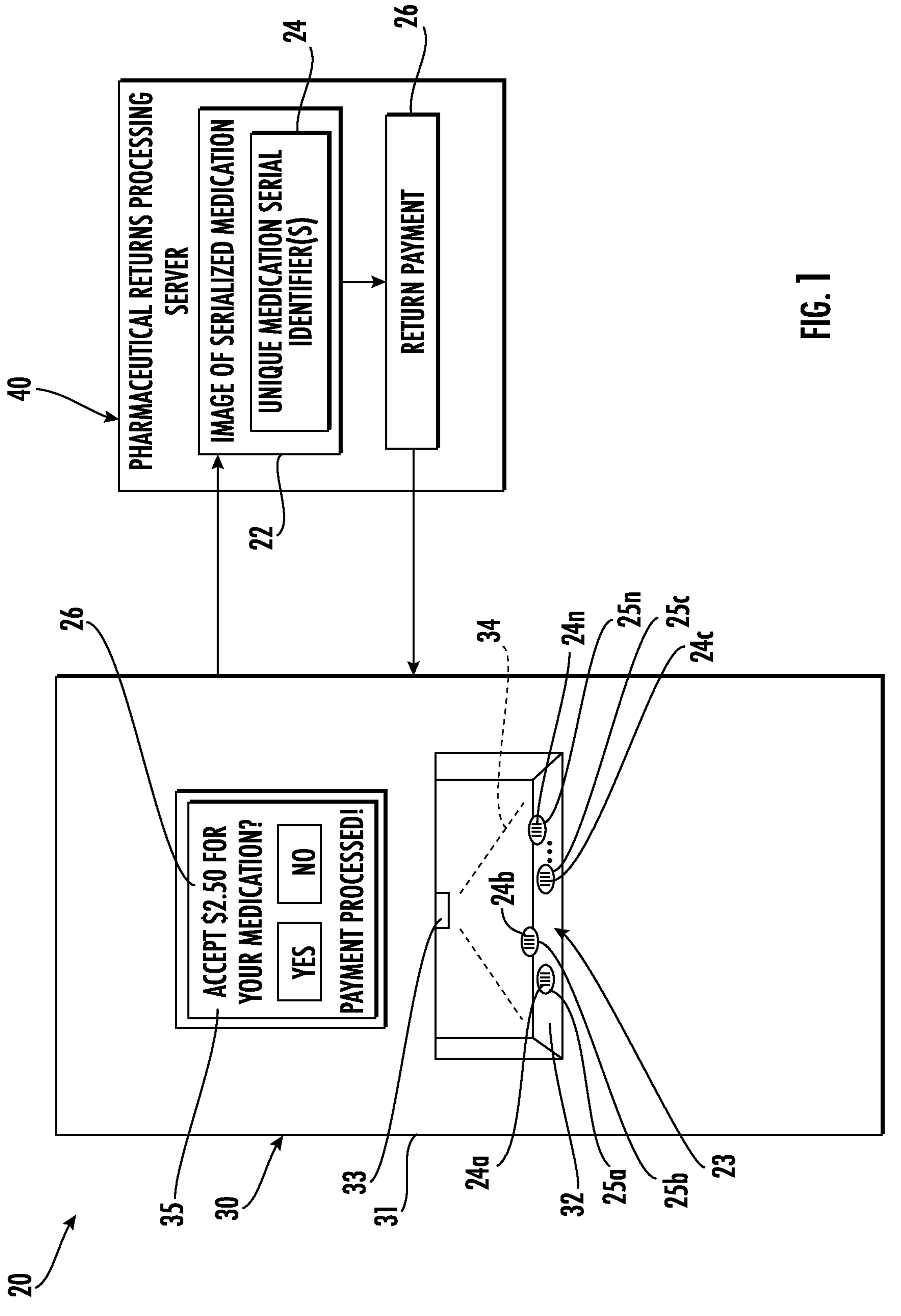
FIG. 1 is a schematic diagram of a pharmaceutical returns processing system in accordance with an embodiment.
Figure 2:
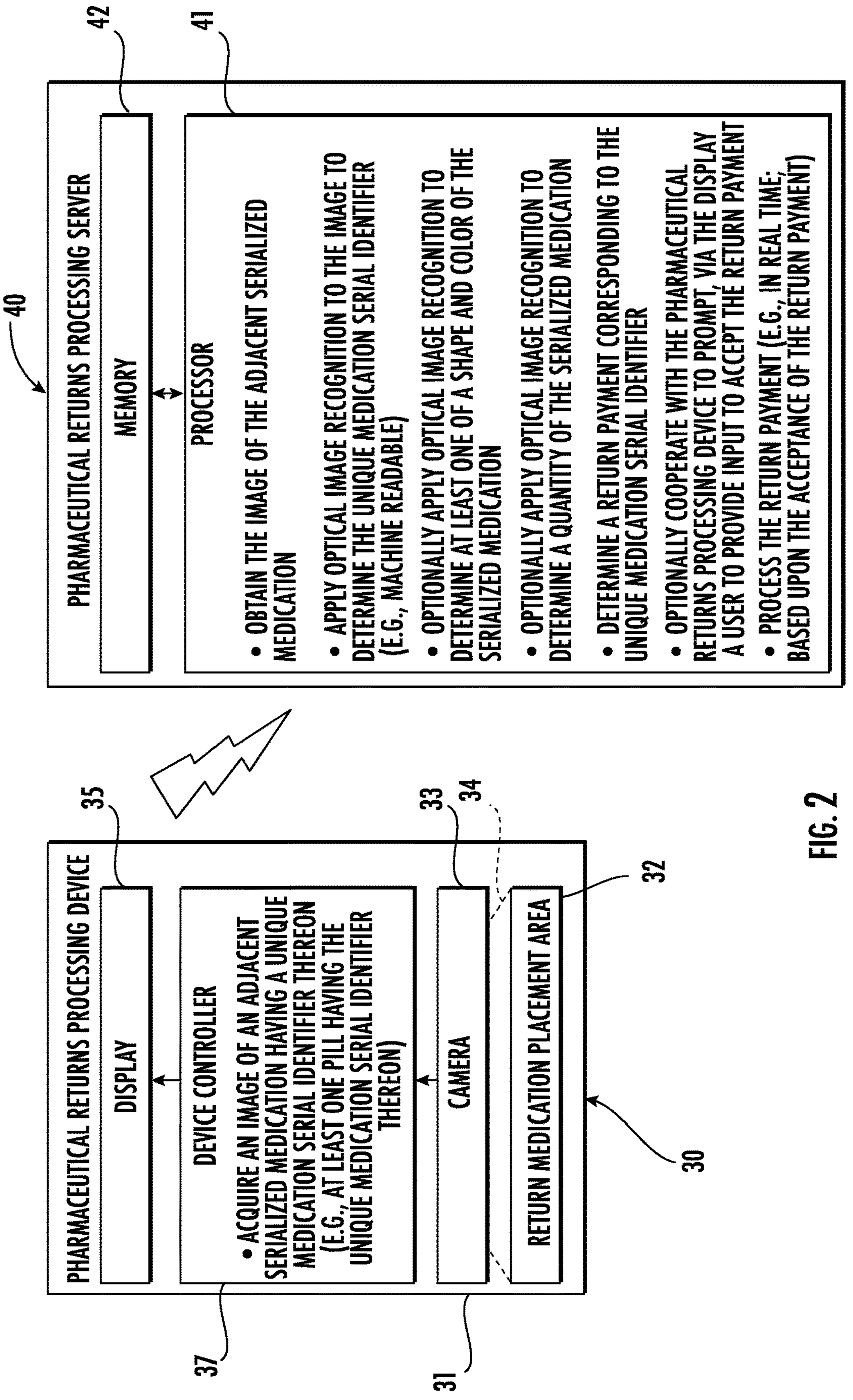
FIG. 2 is a schematic block diagram of the pharmaceutical returns processing system of FIG. 1.

Referring initially to FIGS. 1 and 2 a pharmaceutical returns processing system 20 includes a pharmaceutical returns processing device 30. The pharmaceutical returns processing device 30 illustratively includes a housing 31 defining a return medication placement area 32 for placement of a serialized medication adjacent thereto.

The pharmaceutical returns processing device 30 also includes a camera 33 carried by the housing 31. The camera 33 has the return medication placement area 32 within the field of view 34 of the camera. The pharmaceutical returns processing device 30 also includes a device controller 37 coupled to the camera 33. The pharmaceutical returns processing device 30 also illustratively includes a display 35 carried by the housing 31 and coupled to the device controller 37. Accordingly, the pharmaceutical returns processing device 30 is illustratively in the form of a kiosk, for example, that may be located at a pharmacy or other store where medications may be dispensed and/or returned. Of course, the pharmaceutical returns processing device 30 may be in the form of another type of device, for example, a desktop or tabletop device.

The device controller 37 cooperates with the camera 33 to acquire an image 22 of an adjacent serialized medication 23 having a unique medication serial identifier 24 thereon. The unique medication serial identifier 24 may be in the form of a machine-readable code, for example, a barcode or QR code. The unique medication serial identifier 24 may include alphanumeric characters printed on the serialized medication 23. The serialized medication 23 may be in the form of one or more serialized pills 25*a*-25*n*, each having a unique medication serial identifier thereon 24*a*-24*n*.

The pharmaceutical returns processing system 20 also includes a pharmaceutical returns processing server 40. The pharmaceutical returns processing server 40 includes a processor 41 and an associated memory 42. While operations of the pharmaceutical returns processing server 40 are described herein, it should be understood by those skilled in the art that the operations are performed by way of cooperation between the processor 41 and the memory 42. Additionally, those skilled in the art will appreciate that the pharmaceutical returns processing server 40 may be remote from the pharmaceutical returns processing device 30 or part of the pharmaceutical returns processing device (e.g., carried by the housing 31).

Figure 3:
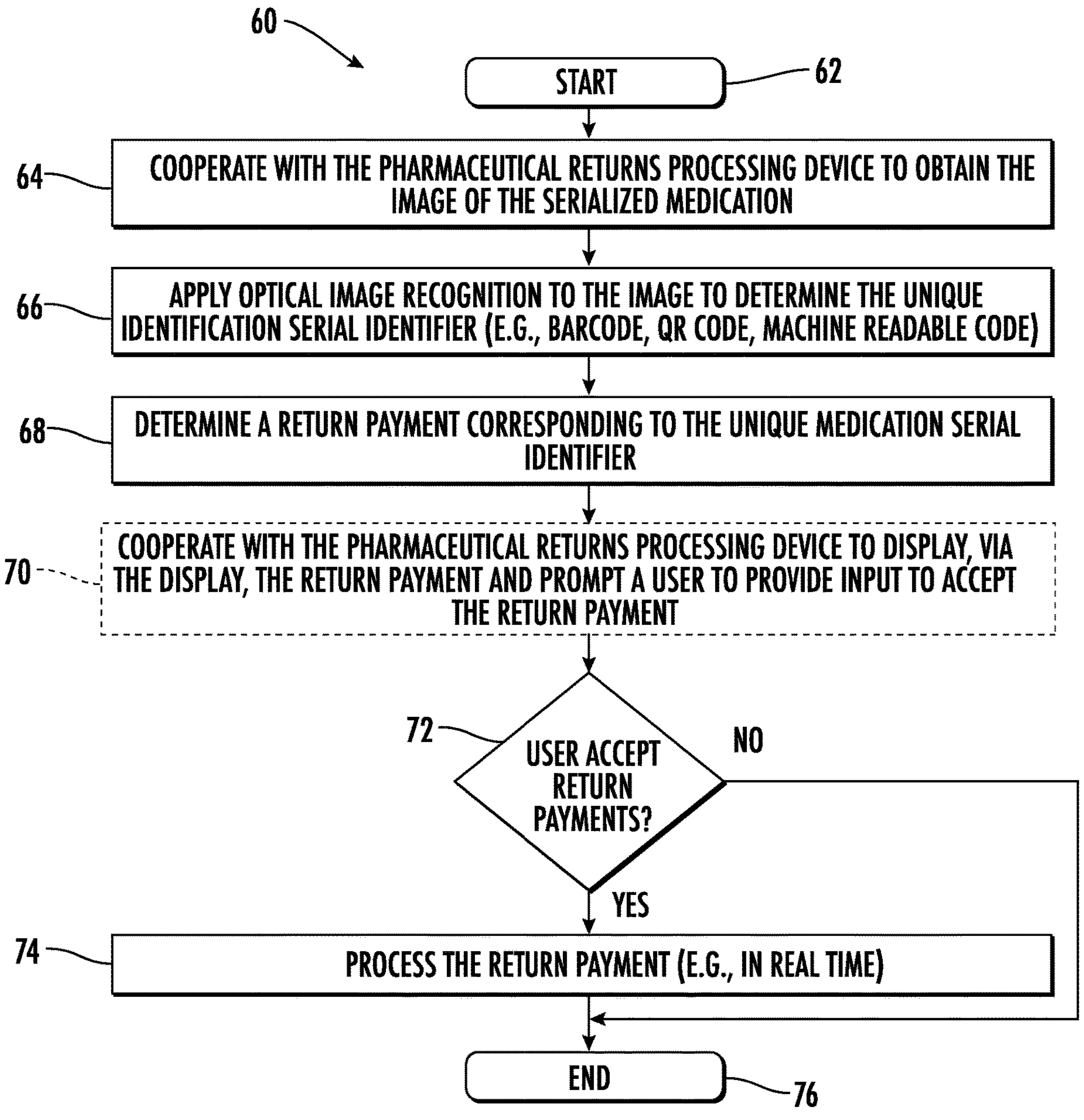
FIG. 3 is a flow diagram illustrating operation of the pharmaceutical returns processing server of FIG. 1.

Referring now to the flowchart 60 in FIG. 3, beginning at Block 62, operation of the pharmaceutical returns processing server 40 will now be described. At Block 64, the pharmaceutical returns processing server 40 cooperates with the pharmaceutical returns processing device 30 to obtain the image 22 of the serialized medication 23. The image 22 may be wirelessly communicated between the pharmaceutical returns processing device 30 and the pharmaceutical returns processing server 40, for example.

The pharmaceutical returns processing server 40 applies optical image recognition to the image 22 to determine the unique medication serial identifier 24, for example, by identifying the barcode, alphanumeric characters, and/or QR code (Block 66). The unique medication serial identifier 24 may be compared to a database of stored identifiers to determine what serialized medication is adjacent or in the return medication placement area 32.

Optical image recognition may also be applied to determine one or more of the color and shape of the serialized medication 23. For example, optical image recognition may be used to determine boundaries of each individual serialized pill 25*a*-25*n* by comparing adjacent pixels in the image 22. The individual pixels may be examined for color and to determine boundaries, for example, where two colors meet. The color and/or shape, for example, based upon the optical image recognition may be compared to colors and shapes of known serialized medications stored in a database, for example, the memory 42.

Optical image recognition may also be applied to the image 22 to determine a quantity of the serialized medication 23. For example, the pharmaceutical returns processing server 40 may identify multiple unique medication serial identifiers 24*a*-24*n* in the image 22 and, based thereon, determine the quantity of the serialized medication 23. Other and/or additional techniques may be used to determine the quantity of the serialized medication 23, for example, counting pixel boundaries and/or applying boundary algorithms to the image 22, which may be segmented for quicker processing and increase ease of boundary determinations.

At Block 68, the pharmaceutical returns processing server 40 determines a return payment 26 corresponding to the unique medication serial identifier 24. For example, for a given serialized medication 23, the pharmaceutical returns processing server 40 may determine that each pill 25*a*-25*n* may have a return value, for example, $0.50 per pill. The pharmaceutical returns processing server 40 may determine the return payment 26 based upon the determined quantity. Thus, for example, for five pills, the return payment 26 may be $2.50. The value of each pill 25*a*-25*n* or of the given serialized medication 23 may be determined based upon a lookup table, for example, stored in a database in the memory 42. Of course, the lookup table may be stored elsewhere, or the pharmaceutical returns processing server 40 may determine the return payment by way of an application programming interface (API) call to a remote pricing server, for example. The color and/or shape may also be used as a basis for determining the return payment 26. For example, the color and/or shape may be in conjunction with the unique medication serial identifier 24 to determine the return payment, particularly where the color and/or shape may be used to identify the serialized medication 23 or a condition of the serialized medication, for example, that may affect the return payment 26.

At Block 70, pharmaceutical returns processing server 40 cooperates with the pharmaceutical returns processing device 30 to display, via the display 35, the return payment 26 and prompt a user to provide input to accept the return payment. If the user accepts the return payment 26, at Block 72, for example, by providing input indicative of acceptance of the return payment the pharmaceutical returns processing server 40 processes the return payment 26 (Block 74). The pharmaceutical returns processing server 40 may process the return payment 26 by communicating with a payment processing server to initiate a transfer of funds to the user (e.g., via a bank account, payment card credit, etc.). The pharmaceutical returns processing server 40 may process the return payment 26 in real time or in near real time, for example, as will be appreciated by those skilled in the art.

The pharmaceutical returns processing server 40 may provide a credit to a payment card associated with the user, provide a credit to a loyalty account associated with the user, or generate and communicate a coupon having a redeemable value equal to the return payment 26. The coupon may be a paper coupon, for example, printed at the pharmaceutical returns processing device 30 or a digital coupon, for example, that may be saved to a digital wallet associated with the user. The pharmaceutical returns processing server 40 may cooperate with the pharmaceutical returns processing device 30 to dispense cash therefrom. Operations end at Block 76.

Figure 4:
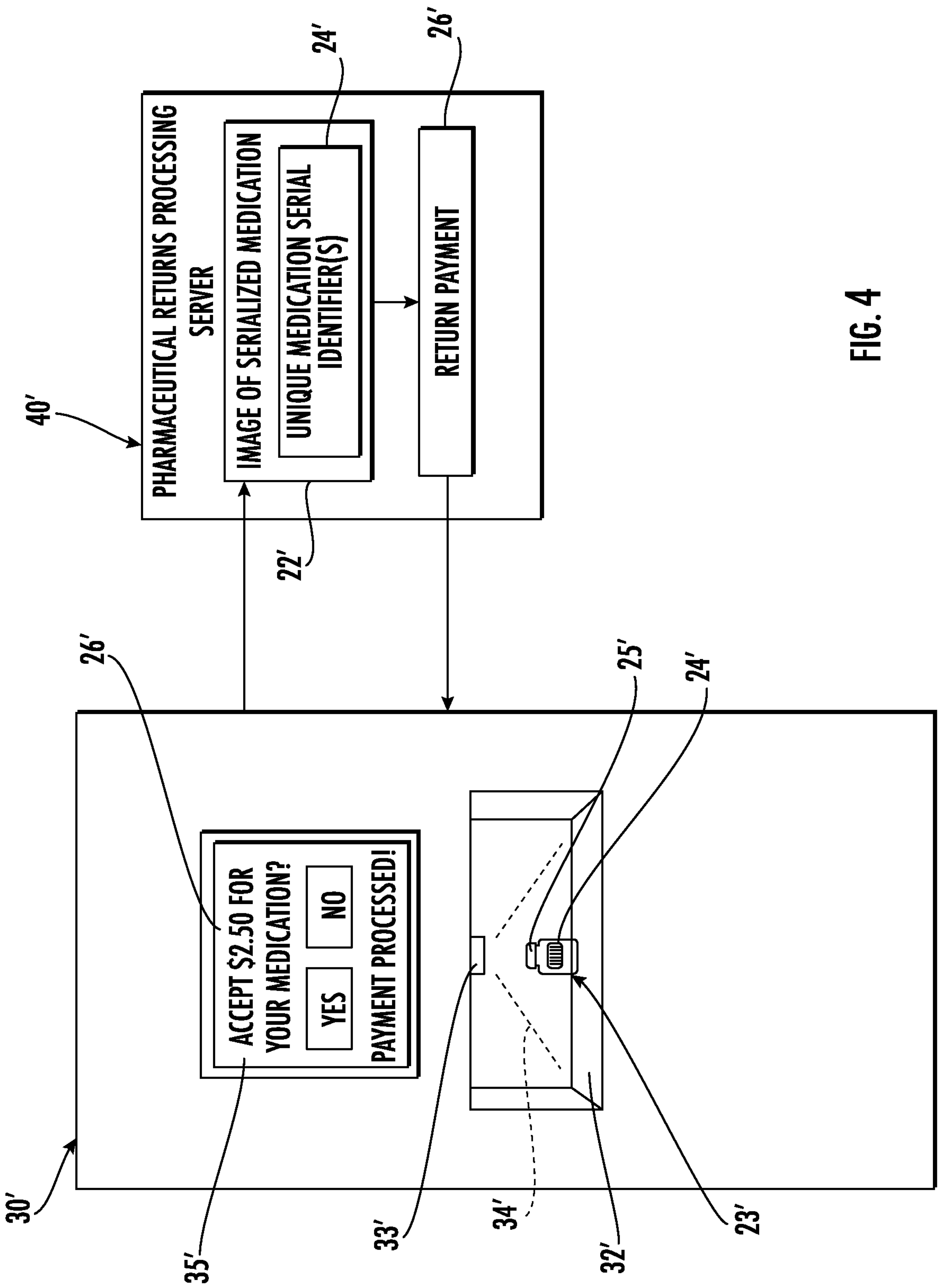
FIG. 4 is a schematic diagram of a pharmaceutical returns processing system in accordance with another embodiment.

Referring now briefly to FIG. 4, the serialized medication 23' may include a serialized medication container 25' that has the unique medication serial identifier 24' thereon. The pharmaceutical returns processing server 40' may thus apply optical image recognition to the image 22' of the serialized medication 23' to determine the unique medication serial identifier 24', which may be on, e.g., printed, the serialized medication container 25'. The serialized medication container 25' may be placed within the field of view 34' of the camera 33' and within the return medication placement area 32". The shape and color of the serialized medication container 25' may thus be used to determine and display, on the display 35' of the pharmaceutical returns processing device 30' the return payment 26', for example, using the techniques described above.

Figure 5:
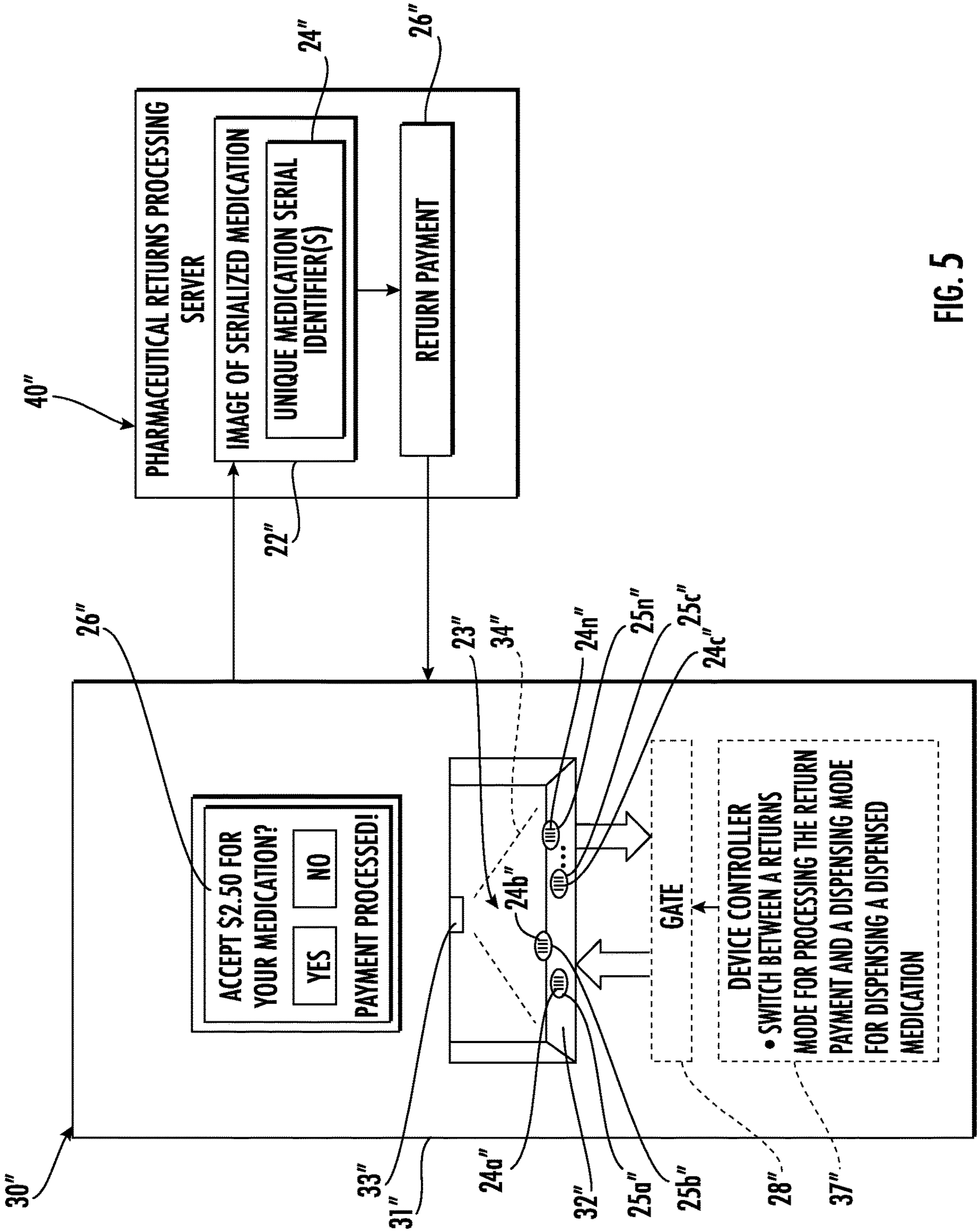
FIG. 5 is a schematic diagram of a pharmaceutical returns processing system in accordance with another embodiment.

Referring now to FIG. 5, in another embodiment, the pharmaceutical returns processing server 40" may be switchable between a returns mode for determining the return payment 26", and a dispensing mode for dispensing a dispensed medication. More particularly, in the present embodiment, the pharmaceutical returns processing device 30" includes a gate 28" carried by the housing 31", coupled to and controllable by the device controller 37", and in communication with the return medication placement area 32". For example, when the pharmaceutical returns processing device 30" is located at a pharmacy, the pharmaceutical returns processing device may be used to dispense a medication. In this case, the pharmaceutical returns processing server 40" may accept as input a medication to dispense, and the cooperate with the pharmaceutical returns processing device 30" to operate the gate 28" to couple to a medication source. Upon dispensing, the camera 33" may be used in cooperation with the pharmaceutical returns processing server 40" to verify the dispensed medication within the field of view 34" of the return medication placement area 32", for example, using the techniques described above to identify the medication or determine the unique medication serial identifier 24" illustratively in the form of serialized pills **25*a*"-25*n*" each including a respective unique medication serial identifier 24*a*"-24*n*" (e.g., when the dispensed medication is a serialized medication). In the returns mode, the pharmaceutical returns processing server 40" operates as described above to cooperate with the pharmaceutical returns processing device 30" which acquires the image 22" of the adjacent serialized medication 23", apply optical image recognition, and determine and process the return payment 26"**. Further details of processing and dispensing medications can be found in U.S. Pat. No. 10,733,578 and U.S. Patent Application Publication No. 2020/0342422, the entire contents of each of which have been incorporated by reference.

A method aspect is directed to a method of processing a pharmaceutical return. The method includes using a pharmaceutical returns processing server 40 to apply optical image recognition to an image 22 to determine a unique medication serial identifier 24. The image 22 is acquired by a pharmaceutical returns processing device 30 and may be of an adjacent serialized medication 23 having the unique medication serial identifier 24 thereon. The method includes using the pharmaceutical returns processing server 40 to determine a return payment 26 corresponding to the unique medication serial identifier 24, and process the return payment.

A computer readable medium aspect is directed to a non-transitory computer readable medium for processing a pharmaceutical return. The non-transitory computer readable medium has computer executable instructions that when executed by a processor 41 cause the processor to perform operations. The operations include applying optical image recognition to an image 22 to determine a unique medication serial identifier 24, the image being acquired by a pharmaceutical returns processing device 30 and being of an adjacent serialized medication 23 having the unique medication serial identifier thereon. The operations include determining a return payment 26 corresponding to the unique medication serial identifier 24, and processing the return payment.

While several embodiments have been described herein, it should be appreciated by those skilled in the art that any element or elements from one or more embodiments may be used with any other element or elements from any other embodiment or embodiments. Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A pharmaceutical returns processing system comprising:

a pharmaceutical returns processing device comprising
- a housing defining a medication placement area,
- a camera carried by the housing and having a field of view including the medication placement area,
- a medication source carried by the housing,
- a gate carried by the housing and coupled to the medication source, and
- a controller coupled to the gate and the camera, and configured to acquire one of an image of a serialized medication within the medication placement area and having a unique medication serial identifier thereon, and an image of a dispensed medication; and a pharmaceutical returns processing server switchable between a returns mode for determining a return payment and a dispensing mode for dispensing the dispensed medication, the pharmaceutical returns processing server configured to operate in the dispensing mode to selectively operate the gate to couple the medication source to the medication placement area for dispensing of the dispensed medication into the medication placement area, apply optical image recognition to the image of the dispensed medication, and verify the dispensed medication within the medication placement area, and operate in the returns mode to selectively operate the gate to decouple the medication source from the medication placement area, apply optical image recognition to the image of the serialized medication to determine the unique medication serial identifier, determine the return payment corresponding to the unique medication serial identifier, and process the return payment.

2. The pharmaceutical returns processing system of claim 1 wherein the pharmaceutical returns processing device comprises a display carried by the housing; and wherein the pharmaceutical returns processing server is configured to cooperate with the pharmaceutical returns processing device to prompt, via the display, a user to provide input to accept the return payment, and process the return payment based upon the input indicative of acceptance of the return payment.

3. The pharmaceutical returns processing system of claim 1 wherein the pharmaceutical returns processing server is configured to apply optical image recognition to the image to determine at least one of a shape and a color of the serialized medication, and determine the return payment based thereon.

4. The pharmaceutical returns processing system of claim 1 wherein the pharmaceutical returns processing server is configured to apply optical image recognition to the image to determine a quantity of the serialized medication, and determine the return payment based upon the quantity.

5. The pharmaceutical returns processing system of claim 1 wherein the serialized medication comprises at least one serialized pill having the unique medication serial identifier thereon.

6. The pharmaceutical returns processing system of claim 1 wherein the unique medication serial identifier comprises a machine readable unique medication serial identifier code.

7. The pharmaceutical returns processing system of claim 1 wherein the pharmaceutical returns processing server is configured to process the return payment in real time.

8. A pharmaceutical returns processing server comprising:

a processor and an associated memory configured to switch between a returns mode for determining a return payment and a dispensing mode for dispensing a dispensed medication, operate in the dispensing mode to selectively operate a gate carried by a housing of a pharmaceutical returns processing device to couple a medication source carried by the housing to a medication placement area defined by the housing for dispensing of the dispensed medication into the medication placement area, apply optical image recognition to an image of the dispensed medication, the image of the dispensed medication acquired by a camera carried by the housing of the pharmaceutical returns processing device, and verify the dispensed medication within the medication placement area, operate in the returns mode to selectively operate the gate to decouple the medication source from the medication placement area, apply optical image recognition to an image of a serialized medication to determine a unique medication serial identifier, the image of the serialized medication acquired by the camera of the pharmaceutical returns processing device when placed in the medication placement area, the serialized medication having the unique medication serial identifier thereon, determine the return payment corresponding to the unique medication serial identifier, and process the return payment.

9. The pharmaceutical returns processing server of claim 8 wherein the processor is configured to apply optical image recognition to the image to determine at least one of a shape and a color of the serialized medication, and determine the return payment based thereon.

10. The pharmaceutical returns processing server of claim 8 wherein the processor is configured to apply optical image recognition to the image to determine a quantity of the serialized medication, and determine the return payment based upon the quantity.

11. A pharmaceutical returns processing device comprising:

a housing defining a medication placement area for one of placement of a serialized medication having a unique medication serial identifier thereon and dispensing of a dispensed medication;

a camera carried by the housing and having the medication placement area within a field of view of the camera;

a medication source carried by the housing;

a gate carried by the housing and coupled to the medication source; and a controller coupled to the gate and the camera and configured to acquire one of an image of the serialized medication within the return medication placement area and an image of the dispensed medication, and communicate the one of the image of the serialized medication and the dispensed medication to a pharmaceutical returns processing server switchable between a returns mode for determining a return payment and a dispensing mode for dispensing the dispensed medication, the communication causing to cause the pharmaceutical returns processing server to operate in the dispensing mode to selectively operate the gate to couple the medication source to the medication placement area for dispensing of the dispensed medication into the medication placement area, apply optical image recognition to the image of the dispensed medication, and verify the dispensed medication within the medication placement area, and operate in the returns mode to decouple the medication source from the medication placement area, apply optical image recognition to the image of the serialized medication to determine the unique medication serial identifier, determine the return payment corresponding to the unique medication serial identifier, and process the return payment.

12. The pharmaceutical returns processing device of claim 11 further comprising a display carried by the housing;

and wherein the controller is configured to cooperate with the pharmaceutical returns processing server to display a prompt on the display for user input to accept the return payment, and cause the pharmaceutical returns processing server to process the return payment based upon the input indicative of acceptance of the return payment.

13. A method of processing a pharmaceutical return comprising:

using a pharmaceutical returns processing server to switch between a returns mode for determining a return payment and a dispensing mode for dispensing a dispensed medication, operate in the dispensing mode to selectively operate a gate carried by a housing of a pharmaceutical returns processing device to couple a medication source carried by the housing to a medication placement area defined by the housing for dispensing of the dispensed medication into the medication placement area, apply optical image recognition to an image of the dispensed medication, the image of the dispensed medication acquired by a camera carried by the housing of the pharmaceutical returns processing device, and verify the dispensed medication within the medication placement area, operate in the returns mode to selectively operate the gate to decouple the medication source from the medication placement area, apply optical image recognition to an image of a serialized medication to determine a unique medication serial identifier, the image of the serialized medication acquired by the camera of the pharmaceutical returns processing device when placed in the medication placement area, the serialized medication having the unique medication serial identifier thereon, determine the return payment corresponding to the unique medication serial identifier, and process the return payment.

14. The method of claim 13 wherein using the pharmaceutical returns processing server comprises using the pharmaceutical returns processing server to apply optical image recognition to the image to determine at least one of a shape and a color of the serialized medication, and determine the return payment based thereon.

15. The method of claim 13 wherein using the pharmaceutical returns processing server comprises using the pharmaceutical returns processing server to apply optical image recognition to the image to determine a quantity of the serialized medication, and determine the return payment based upon the quantity.

16. A non-transitory computer readable medium for processing a pharmaceutical return, the non-transitory computer readable medium having computer executable instructions that when executed by a processor cause the processor to perform operations comprising:

switching between a returns mode for determining a return payment and a dispensing mode for dispensing a dispensed medication;

operating in the dispensing mode to selectively operate a gate carried by a housing of a pharmaceutical returns processing device to couple a medication source carried by the housing to a medication placement area defined by the housing for dispensing of the dispensed medication into the medication placement area, apply optical image recognition to an image of the dispensed medication, the image of the dispensed medication acquired by a camera carried by the housing of the pharmaceutical returns processing device, and verify the dispensed medication within the medication placement area, operating in the returns mode to selectively operate the gate to decouple the medication source from the medication placement area, apply optical image recognition to an image of the serialized medication to determine a unique medication serial identifier, the image of the serialized medication acquired by the camera of the pharmaceutical returns processing device when placed in the medication placement area, the serialized medication having the unique medication serial identifier thereon, determine a return payment corresponding to the unique medication serial identifier, and process the return payment.

17. The non-transitory computer readable medium of claim 16 wherein the operations comprise applying optical image recognition to the image to determine at least one a shape and a color of the serialized medication, and determining the return payment based thereon.

18. The non-transitory computer readable medium of claim 16 wherein the operations comprise applying optical image recognition to the image to determine a quantity of the serialized medication, and determining the return payment based upon the quantity.

* * * * *